US00PP37482P2

(12) United States Plant Patent
Koot

(10) Patent No.: US PP37,482 P2
(45) Date of Patent: Jun. 23, 2026

(54) ***EUPHORBIA* PLANT NAMED 'Doeupstaduwhifla25'**

(50) Latin Name: *Euphorbia chamaesyce*
Varietal Denomination: Doeupstaduwhifla25

(71) Applicant: DUMMEN GROUP B.V., De Lier (NL)

(72) Inventor: Arjan Koot, Oeffelt (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 19/054,179

(22) Filed: Feb. 14, 2025

(51) Int. Cl.
*A01H 5/12* (2018.01)
*A01H 6/38* (2018.01)

(52) U.S. Cl.
USPC ..... Plt./302

(58) Field of Classification Search
USPC ..... Plt./302
See application file for complete search history.

(56) References Cited

U.S. PATENT DOCUMENTS

PP32,682 P3 * 12/2020 Hofmann ..... A01H 6/385
Plt./302

* cited by examiner

*Primary Examiner* — Susan Mccormick Ewoldt
*Assistant Examiner* — Zachariah Allan Kay
(74) *Attorney, Agent, or Firm* — C. Anne Whealy

(57) ABSTRACT

A new and distinct cultivar of *Euphorbia* plant named 'Doeupstaduwhifla25', characterized by its relatively compact, mounding to outwardly spreading and eventually semi-trailing plant habit; freely branching habit; freely flowering habit; and inflorescences with multiple white-colored flower bracts.

1 Drawing Sheet

Botanical designation: *Euphorbia chamaesyce*.
Cultivar denomination: 'DOEUPSTADUWHIFLA25'.

BACKGROUND OF THE INVENTION

The present invention relates to a new and distinct cultivar of *Euphorbia* plant, botanically known as *Euphorbia chamaesyce* and hereinafter referred to by the name 'Doeupstaduwhifla25'.

The new *Euphorbia* plant is a product of a planned breeding program conducted by the Inventor in Rheinberg, Germany. The objective of the program is to create and develop new freely branching and dense *Euphorbia* plants with mounding plant habit and numerous white-colored flowers per plant.

The new *Euphorbia* plant originated from a self-pollination by the Inventor in August 2019 of a proprietary selection of *Euphorbia chamaesyce* identified as code number EW19-K0010, not patented. The new *Euphorbia* plant was discovered and selected by the Inventor as a single flowering plant within the progeny of the stated self-pollination in a controlled greenhouse environment in Rheinberg, Germany in April 2020.

Asexual reproduction of the new *Euphorbia* plant by terminal vegetative cuttings in a controlled greenhouse environment in Rheinberg, Germany since April 2020 has shown that the unique features of this new *Euphorbia* plant are stable and reproduced true to type in successive generations of asexual reproduction.

SUMMARY OF THE INVENTION

Plants of the new *Euphorbia* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Doeupstaduwhifla25'. These characteristics in combination distinguish 'Doeupstaduwhifla25' as a new and distinct *Euphorbia* plant:

1. Relatively compact, mounding to outwardly spreading and eventually semi-trailing plant habit.
2. Freely branching habit.
3. Freely flowering habit.
4. Inflorescences with multiple white-colored flower bracts.

Plants of the new *Euphorbia* differ primarily from plants of the parent selection in plant habit as plants of the new *Euphorbia* are more compact and denser than and not as large and open as plants of the parent selection.

Plants of the new *Euphorbia* can be compared to plants of the *Euphorbia chamaesyce* 'Inchadiacl', disclosed in U.S. Plant Pat. No. 32,682. In side-by-side comparisons, plants of the new *Euphorbia* differ primarily from plants of 'Inchadiacl' in the following characteristics:

1. Plants of the new *Euphorbia* are more compact than plants of 'Inchadiacl'.
2. Plants of the new *Euphorbia* are sturdier than plants of 'Inchadiacl'.
3. Plants of the new *Euphorbia* flower earlier than plants of 'Inchadiacl'.
4. Inflorescences of plants of the new *Euphorbia* have more flower bracts than inflorescences of plants of 'Inchadiacl'.

5. Flower bracts of inflorescences of plants of the new *Euphorbia* are larger than flower bracts of inflorescences of plants of 'Inchadiacl'.

BRIEF DESCRIPTION OF THE PHOTOGRAPH

The accompanying colored photograph illustrates the overall appearance of the new *Euphorbia* plant showing the colors as true as it is reasonably possible to obtain in colored reproductions of this type. Colors in the photograph may differ slightly from the color values cited in the detailed botanical description which accurately describe the colors of the new *Euphorbia* plant.

The photograph is a side perspective view of a typical flowering plant of 'Doeupstaduwhifla25' grown in a container.

DETAILED BOTANICAL DESCRIPTION

The aforementioned photograph and following observations and measurements describe plants grown during the spring and summer in 22-cm containers in a glass-covered greenhouse in Rheinberg, Germany and under cultural practices typical of commercial *Euphorbia* production. During the production of the plants, day and night temperatures averaged 18° C. and light levels averaged 4,500 lux. Plants were twelve weeks from planting rooted young plants when the photograph was taken and 25 weeks from planting rooted young plants when the description was taken. In the following description, color references are made to The Royal Horticultural Society Colour Chart, Fifth Edition, except where general terms of ordinary dictionary significance are used.

Botanical classification: *Euphorbia chamaesyce* 'Doeupstaduwhifla25'.

Parentage:

*Female, or seed, parent*.—Proprietary selection of *Euphorbia chamaesyce* identified as code number EW19-K0010, not patented.

*Male, or pollen, parent*.—Proprietary selection of *Euphorbia chamaesyce* identified as code number EW19-K0010, not patented.

Propagation:

*Type*.—Terminal vegetative cuttings.

*Time to initiate roots, summer*.—About five days at temperatures about 20° C.

*Time to initiate roots, winter*.—About seven days temperatures about 20° C.

*Time to produce a rooted young plant, summer*.—About three weeks at temperatures about 20° C.

*Time to produce a rooted young plant, winter*.—About four weeks at temperatures about 20° C.

*Root description*.—Fine, fibrous; typically white in color, actual color of the roots is dependent on substrate composition, water quality, fertilizer type and formulation, substrate temperature and physiological age of roots.

*Rooting habit*.—Freely branching; dense.

Plant description:

*Plant and growth habit*.—Relatively compact, mounding to outwardly spreading and eventually semi-trailing plant habit; inflorescences positioned above and beyond the foliar plane.

*Branching habit*.—Freely branching habit; about three to five primary lateral branches each with numerous secondary lateral branches develop per plant.

*Plant height*.—About 18 cm.

*Plant diameter or spread*.—About 34.5 cm.

*Lateral branch description*.—Length: About 16.5 cm. Diameter: About 3 mm. Internode length: About 2.1 cm. Aspect: Initially upright to outwardly spreading and eventually semi-trailing. Texture and luster: Smooth, glabrous; slightly glossy. Color: Close to 137A.

*Leaf description*.—Arrangement: Opposite, simple. Length: About 3.7 cm. Width: About 9 mm. Shape: Elliptic. Apex: Acute. Base: Attenuate with acute tendencies. Margin: Entire, not lobed. Venation pattern: Pinnate. Texture and luster, upper surface: Pubescent; not rugose; somewhat glossy. Texture and luster, lower surface: Pubescent; rugose; slightly glossy. Color: Developing leaves, upper surface: Close to 144A. Developing leaves, lower surface: Close to 144B. Fully developed leaves, upper surface: Close to N137D; venation, close to 143C. Fully developed leaves, lower surface: Close to 138B; venation, close to 143C. Petioles: Length: About 1.4 cm. Diameter: About 1 mm. Texture and luster, upper and lower surfaces: Pubescent; slightly glossy. Color, upper and lower surfaces: Close to 143C.

Inflorescence description:

*Inflorescence type and habit*.—Inflorescences are composed of a single cyathia surrounded with numerous flower bracts subtending the cyathia; inflorescences positioned above and beyond the foliar plane; freely flowering habit with at least 1,000 inflorescences developing per plant during the flowering season; inflorescences face mostly upright to outwardly.

*Fragrance*.—None detected.

*Natural flowering season*.—Plants typically flower during the spring and summer in Germany; depending on temperature, plants typically start flowering about eight weeks after planting rooted young plants.

*Inflorescence longevity*.—Depending on temperatures, inflorescences last about ten days on the plant; inflorescences persistent.

*Flower bracts*.—Quantity per inflorescence: About 75. Length, largest bracts: About 8 mm. Width, largest bracts: About 2.4 mm. Shape: Elliptic to lanceolate. Apex: Rounded to acute. Base: Fused. Margin: Entire, not undulate. Texture and luster, upper and lower surfaces: Smooth, glabrous; slightly glossy to matte. Aspect: Mostly horizontal, flat. Venation pattern: Pinnate. Color: Developing and fully expanded bracts, upper surface: Close to NN155C; venation, close to NN155C; color does not change with subsequent development. Developing and fully expanded bracts, lower surface: Close to NN155D; venation, close to NN155D; color does not change with subsequent development. Flower bract petioles: Length: About 2 mm. Diameter: About 1 mm. Texture and luster, upper and lower surfaces: Smooth, glabrous; slightly glossy. Color, upper and lower surfaces: Close to 144B.

*Cyathia*.—Quantity per inflorescence: One. Diameter: About 2.5 mm. Length: About 4 mm. Shape: Roughly globose. Texture, inner and outer surfaces: Smooth, glabrous. Color, inner surface: Close to 143C. Color, outer surface: Close to 143A.

*Nectaries*.—Quantity per cyathium: One. Length: About 5 mm. Width: About 5 mm. Shape: Oval.

Texture, inner and outer surfaces: Smooth, glabrous. Color, inner and outer surfaces: Close to 144C and 155C.

*Peduncles*.—Length: About 4.4 cm. Diameter: About 1.4 mm. Aspect: Incurved. Texture and luster: Smooth, glabrous; matte. Color: Close to 137B.

*Reproductive organs*.—Stamens: Quantity per cyathia: Six. Filament length: About 1.5 mm. Filament color: Close to NN155C. Anther length: About 0.5 mm. Anther shape: Oval. Anther color: Close to 1C. Pollen color: Close to 162D. Pistils: Quantity per cyathia: One. Pistil length: About 2 mm. Stigma shape: Crested. Stigma color: Close to NN155C. Style length: About 0.5 mm. Style color: Close to NN155C. Ovary color: Close to 143B.

*Seeds and fruits*.—To date, seed and fruit production has not been observed on plants of the new *Euphorbia*.

Pathogen & pest resistance: To date, plants of the new *Euphorbia* have not been shown to be resistant to pathogens and pests common to *Euphorbia* plants.

Temperature tolerance: Plants of the new *Euphorbia* have been observed to tolerate temperatures ranging from 8° C. to 30° C.

It is claimed:

1. A new and distinct *Euphorbia* plant named 'Doeupstaduwhifla25' as herein illustrated and described.

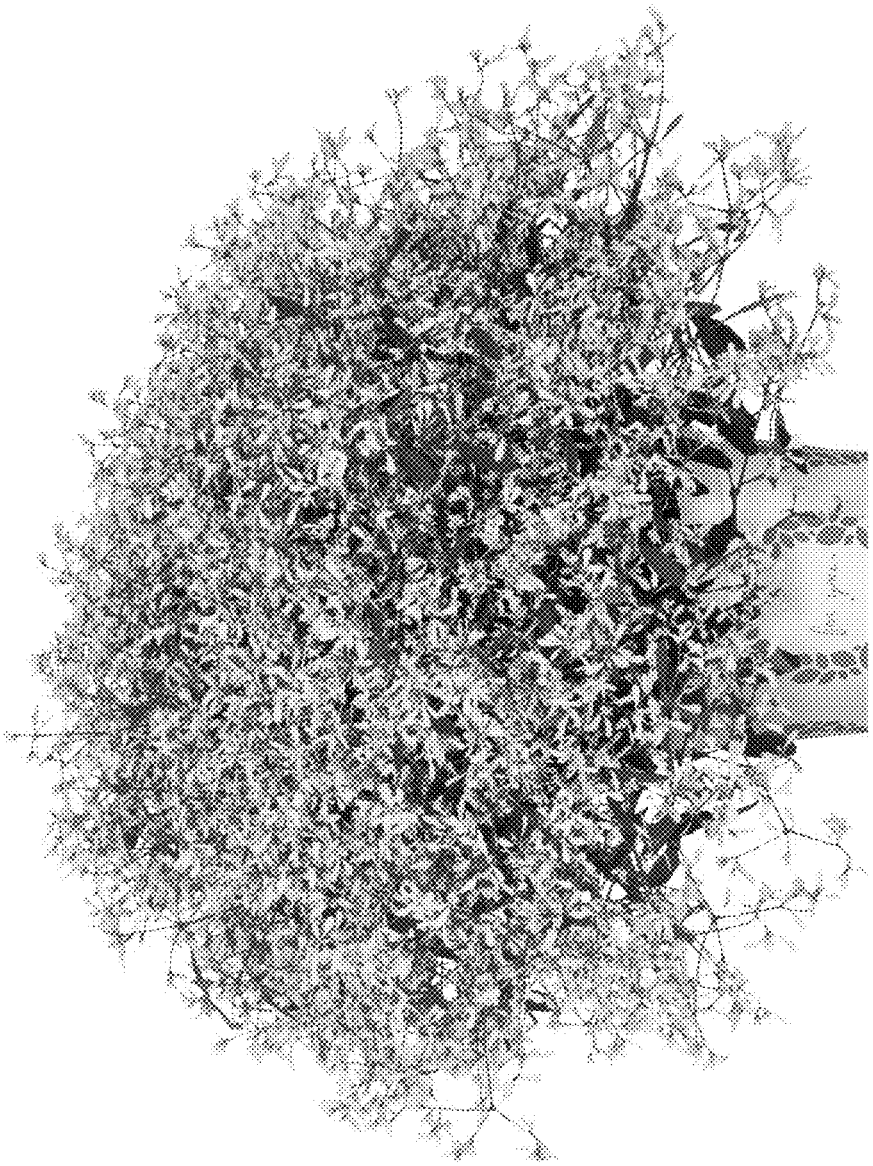

* * * * *